US010603602B2

(12) United States Patent
Macchia et al.

(10) Patent No.: US 10,603,602 B2
(45) Date of Patent: Mar. 31, 2020

(54) COMPONENTS OF A DISTILLATION APPARATUS, METHOD FOR THEIR PRODUCTION AND USES THEREOF

(71) Applicant: GREEN ENGINEERING S.R.L., Colle di Val d'Elsa (Siena) (IT)

(72) Inventors: Eugenio Macchia, Colle di Val d'Elsa (IT); Rolando Barbucci, Monteriggioni (IT); Serena Fedi, Barberino Val d'Elsa (IT); Lorenzo Mencuccini, Torrita di Siena (IT)

(73) Assignee: GREEN ENGINEERING S.R.L., Colle di Val d'Elsa (IT)

( * ) Notice: Subject to any disclaimer, the term of this patent is extended or adjusted under 35 U.S.C. 154(b) by 0 days.

(21) Appl. No.: 14/897,187

(22) PCT Filed: May 21, 2014

(86) PCT No.: PCT/IB2014/061585
§ 371 (c)(1),
(2) Date: Dec. 9, 2015

(87) PCT Pub. No.: WO2014/199252
PCT Pub. Date: Dec. 18, 2014

(65) Prior Publication Data
US 2016/0129368 A1   May 12, 2016

(30) Foreign Application Priority Data

Jun. 10, 2013 (IT) .............................. MI2013A0952

(51) Int. Cl.
*B01D 3/32* (2006.01)
*C12H 6/02* (2019.01)
(Continued)

(52) U.S. Cl.
CPC ............... *B01D 3/32* (2013.01); *B01D 3/001* (2013.01); *B05D 1/005* (2013.01); *B22F 1/0003* (2013.01);
(Continued)

(58) Field of Classification Search
CPC .. B01D 3/32; B01D 3/001; C12H 6/02; C23C 4/08; C23C 4/18; C23C 24/085;
(Continued)

(56) References Cited

U.S. PATENT DOCUMENTS 4,371,623 A   2/1983 Taylor
2007/0036951 A1   2/2007 Nguyen et al.
(Continued)

FOREIGN PATENT DOCUMENTS

BE   725124   5/1969
EP   0459310   12/1991
(Continued)

OTHER PUBLICATIONS

Pot still distillation—2011.*
(Continued)

*Primary Examiner* — Hamid R Badr
(74) *Attorney, Agent, or Firm* — Pearne & Gordon LLP (57) ABSTRACT

The present invention regards a metallic component of a distillation and/or fermentation apparatus, characterized by being covered with at least one layer of nanostructured copper, said layer of nanostructured copper possibly comprising also nano-particles of TiO2. Furthermore, the present invention regards methods for covering said metallic component with at least one layer of nanostructured copper which may also comprise nanoparticles of TiO2. Finally, the present invention regards the use of said components in distillation and/or fermentation processes, in particular for the alcoholic distillation of spirit beverages.

18 Claims, 6 Drawing Sheets (51) Int. Cl.
- *B01D 3/00* (2006.01)
- *C23C 4/08* (2016.01)
- *C23C 4/18* (2006.01)
- *C23C 24/08* (2006.01)
- *C23C 4/131* (2016.01)
- *B05D 1/00* (2006.01)
- *B22F 1/00* (2006.01)
- *C12G 3/02* (2019.01)
- *B82Y 5/00* (2011.01)
- *B82Y 30/00* (2011.01)

(52) U.S. Cl.
CPC ............... *C12G 3/02* (2013.01); *C12H 6/02* (2019.02); *C23C 4/08* (2013.01); *C23C 4/131* (2016.01); *C23C 4/18* (2013.01); *C23C 24/085* (2013.01); *C23C 24/087* (2013.01); *B22F 2301/10* (2013.01); *B22F 2302/25* (2013.01); *B22F 2304/05* (2013.01); *B82Y 5/00* (2013.01); *B82Y 30/00* (2013.01)

(58) Field of Classification Search
CPC ....... C23C 4/131; C23C 24/087; B05D 1/005; B22F 1/0003; C12G 3/02
USPC .......................................................... 426/7
See application file for complete search history.

(56) References Cited

U.S. PATENT DOCUMENTS

| | | | | |
|---|---|---|---|---|
| 2009/0302503 | A1* | 12/2009 | Ruuttu | C23C 14/0611 264/400 |
| 2013/0048506 | A1* | 2/2013 | Chen | C10G 2/50 205/317 |
| 2013/0334104 | A1 | 12/2013 | Halas et al. | |

FOREIGN PATENT DOCUMENTS

| | | |
|---|---|---|
| GB | 2457186 | 8/2009 |
| WO | 9961125 A1 | 12/1999 |
| WO | 2012082364 A1 | 6/2012 |

OTHER PUBLICATIONS

Li, C. et al. Nanostructured copper interfaces for enhanced boiling. 2008—Abstract.*

Paradies, H. H. et al. 2000. The Rigaku J. 17: 9-19 (Year: 2000).*

* cited by examiner

COMPONENTS OF A DISTILLATION APPARATUS, METHOD FOR THEIR PRODUCTION AND USES THEREOF

TECHNICAL FIELD

The present invention regards a metallic component of a distillation and/or fermentation apparatus and methods for producing said metallic component. In particular, said metallic component is chosen from among: distillation trays, valves for distillation trays, structured packings or random packings, pot stills or pot still parts, dephlegmators, infusers, scrubber columns, evaporators, distillation columns, demisters, containers, tubes and valves for distillation apparatus, shell and tube heat exchangers, plate heat exchangers, reboilers, condensers, filters, lyne arms and fermenters. Furthermore, the present invention regards the use of said metallic components in distillation and/or fermentation processes, in particular, in the alcoholic distillation of spirit beverages, preferably rum, whisky, cognac, grappa, brandy, vodka, tequila, raki, ouzo, whiskey, bourbon, aquavit, extra neutral alcohol, neutral alcohol and in general any other spirit beverage or alcohol hereafter added to a beverage.

Distillation is a universe rich in history, traditions and human ingenuity which over the course of the centuries has succeeded in perfecting an ancient technique for extracting alcohol from fermented musts starting from diverse sugary raw materials, such as grapes, sugar cane and sugar beet, or from starchy raw materials, such as cereals and potatoes. Every people has exploited what the land offered to obtain beverages with a high alcohol content, using the mechanism which is at the base of all distillation, i.e. the different boiling points of the components of a mixture. Typically alcoholic distillation can be carried out continuously (with distillation columns) or discontinuously (with pot stills).

The oldest method is discontinuous distillation which requires the use of pot stills. According to this procedure the mixture to be distilled is loaded into the pot still where, as the temperature rises, the most volatile compound tends to evaporate first, and thus the vapour which is created is richer in the more volatile compound, while the liquid phase is richer in the less volatile compound. The vapour rich in alcohol then flows through a condenser which brings it back to the liquid state in a collecting container. This liquid rich in alcohol constitutes the product of the distillation process. The liquid which remains in the still, impoverished of the more volatile compound, constitutes the waste of the process and is discharged from the bottom of the still. When distillation is finished, the pot still is charged with a new load to produce the next batch of product.

Modern plants are very often based on the process of continuous distillation in which, instead of pot stills, one or more fractionating columns (also known as distillation columns) are used, which are continuously fed, and from which the product is continuously drawn off.

Distillation columns consist principally of three portions: the shell, i.e. the column proper, which is usually cylindrical or rectangular in shape and is distinguished into a head, which is the highest part of the column, and a bottom, which is the lowest part of the column; the reboiler which provides the heat to the base mixture and which can be integrated directly into the column; and the condenser which cools and condenses the head vapours. Distillation columns are distinguished into plate columns and packing columns.

Plate columns are made up precisely of a series of distillation plates, at which contact occurs between the liquid current and the gas current. The distillation plates are provided with holes and sometimes with specific valves, designed to make the vapour flow upwards and the liquid downwards, trapping a fraction of the liquid phase on the plate.

Inside the distillation column there is a liquid phase and a gas phase which are generally in counterflow contact, i.e. the liquid phase passes through the column from the top downwards, while the gas phase passes through the column from the bottom upwards. At the bottom of the column, part of the liquid current is drawn off while the other part is evaporated by means of the reboiler. Similarly at the head of the column part of the gas current is drawn off while the other part is condensed by the condenser and reintroduced into the column to generate reflux.

At each of the stages of the column a liquid-vapour equilibrium is established between the descending liquid current and the ascending gas current. There being as many equilibriums as there are stages, and since at each stage the "heaviest" components tend to turn into liquid phase, the lighter components accumulate at the head of the column, while the heavier components accumulate at the bottom of the column.

The most widely used materials for making distillation apparatus (stills, plate columns or packing columns) are copper and stainless steel. The use of stainless steel in this sector is fairly recent and is limited mainly to continuous column distillation plants.

The material historically used in the distillation of beverages, in particular for the production of traditional distillates such as rum, whisky, cognac, grappa or brandy, is copper. The choice of copper is correlated with its high thermal conductivity (about 380 W/mK compared with other metals, for example carbon steel with 60 W/mK), which enables distillation cycles to be performed in limited times, and its good workability.

Over time the use of copper in this particular sector has increasingly consolidated, inter alia because it has been scientifically demonstrated that copper performs an action of absorbing undesired substances present in the musts undergoing distillation, and is therefore capable of refining the flavour of the distillate and of reducing undesired aromas.

The whisky industry has been particularly active in this direction and has investigated the effects of adsorption of copper into musts undergoing distillation. This investigation demonstrated that the copper surfaces of distillation apparatus act by capturing mercaptan type compounds, sulphides and ethyl carbamate.

Mercaptans and sulphides impart unpleasant odours to the distillates and therefore the capacity of copper to trap them is very important for the purposes of refining the flavour of traditional distillates. The action of copper on ethyl carbamate is also of considerable importance since this compound is carcinogenic.

However, besides having positive effects on distillates, in particular conditions, copper can also have negative effects on the flavour of distillates due to the release of certain nitrogenous copper compounds. In fact, while completely clean copper surfaces manage to trap mercaptans, ethyl carbamate and other undesired compounds, copper surfaces saturated with these compounds release chemical compounds in which the copper atoms are bonded to nitrogen atoms.

Nitrogenous copper compounds in their turn are potential precursors of the formation of ethyl carbamate in the subsequent stages of the production of distillates, in particular during ageing.

From this point of view the need is particularly felt in the distillation sector, especially in the distillation of beverages, to develop distillation procedures and/or distillation apparatus which make it possible to render more effective and maximize the capture of undesired substances, in particular ethyl carbamate, sulphides and mercaptans.

Furthermore, in the light of the account given above it is obvious that maintaining clean copper surfaces in distillation apparatus is an essential condition for the correct operation of the sequestering activity of copper in relation to molecules capable of altering the flavour of distillates. In particular, cleaning and removal of compounds which form over time on the copper surface of distillation apparatus is essential for the purpose of avoiding the release into the musts of polluting compounds, in particular nitrogenous copper compounds, precursors of ethyl carbamate, which are potentially hazardous to health.

Currently, cleaning the copper surfaces of distillation apparatus is performed by means of intensive cleaning cycles in which citric acid and caustic soda are alternated.

However, this method causes long interruption times to production, entails high consumption and costly disposal of chemical products, and furthermore entails high direct energy consumption (for example pumping the washing solution) and indirect energy consumption (for example shut-down and start-up of production with high steam consumption) and shows limited efficiency in removing the compounds.

The applicant proposes, as a solution to the problems of the known art stated above, the method of the present invention which makes it possible to cover a metallic component of a distillation or fermentation apparatus with layers of nanostructured copper possibly comprising nanoparticles of TiO2.

Advantageously the method of the present invention makes it possible to obtain metallic components of distillation or fermentation apparatuses characterized by a significantly increased ratio between the surface area of the active copper and the geometric surface area of the metal of which the component is made. When applied, therefore, to the distillation or fermentation sector, the metallic components obtained with the method of the present invention display a highly enhanced adsorption capacity, compared with those obtained by traditional metallurgical techniques, against undesired substances such as mercaptans, sulphides and ethyl carbamate present in the mixture during the processes of distillation/fermentation. In this way by using the metallic components of the present invention it is possible to maximize the removal of mercaptans, sulphides and ethyl carbamate which are present during the process of distillation/fermentation and are responsible for altering the flavour of the distillate and hazardous to public health.

Furthermore, the method of the present invention makes it possible to obtain metallic components for distillation and/or fermentation plants which are also easy to clean, in particular they are self-cleaning and self-regenerating.

Thus by using the metallic components of the present invention, it is possible to avoid the long and costly cleaning cycles to which the copper surfaces (saturated with mercaptans, sulphides and ethyl carbamate or other undesired compounds) of currently used distillation apparatuses are subjected. In particular, the Applicant has surprisingly found that with the method of the present invention there is a reduction of about 50% in energy consumption for the washing cycles (CIP—Cleaning in Place).

Using the metallic components of the present invention during the distillation/fermentation processes, environmental pressures are also significantly reduced, in terms of eco-efficient process and product innovation. In fact, the metallic components of the present invention, having an increased capacity for removing substances such as mercaptans, sulphides and ethyl carbamate, and having a more efficient capacity for being cleaned and regenerated, enable a significant reduction in energy expended for cleaning operations (greater energy efficiency) and a smaller polluting load of effluents (minimization of environmental impact due to production activity).

The present invention is described in detail below with the aid of the accompanying drawings, in which.

The present invention concerns a metallic component of a distillation and/or fermentation apparatus covered, totally or partially, by at least one layer of nanostructured copper.

Preferably said layer of nanostructured copper comprises nanoparticles of copper characterized by a diameter ranging from 10 to 50 nanometres (nm), more preferably from 20 to 40 nm.

Preferably said layer of nanostructured copper has a mean thickness ranging from 0.25 to 1 mm, preferably of approximately 0.5 mm.

According to a preferred embodiment of the present invention, the layer of nanostructured copper further comprises nanoparticles of TiO2. Preferably, the nanoparticles of TiO2 are characterized by a diameter ranging preferably from 50 to 200 nm, more preferably from 80 to 150 nm. In the context of the present invention the term 'metallic component' is intended to mean a component consisting essentially of a metal or a component consisting essentially of a metallic alloy.

Preferably said metal is chosen from among: copper, iron, aluminium, titanium and magnesium.

Preferably said alloy is chosen from among: steel (iron-carbon alloy), preferably stainless, bronze, brass and cast iron, aluminium alloys, titanium alloys and magnesium alloys.

In particular, the metallic component is covered with said at least one layer of nanostructured copper by any method known to a person skilled in the art which permits the atomization and/or the ionization of the metallic copper and the deposition of the atomized/ionized copper onto said component, preferably onto the surface of the component which is in contact with the liquid during the distillation/fermentation process.

Preferably, the method used for this purpose is chosen from among the group consisting of: electric arc, thermal embedding, laser assisted embedding, spatially controlled nanoembedding and spraying.

The method particularly preferred for the purposes of the present invention is electric arc.

Said method of electric arc provides preferably at least one stage of melting a source of copper; and/or at least one stage of atomization and/or ionization of the copper, and/or at least one stage of emission of the atomized/ionized copper onto a metallic component of a distillation apparatus, preferably onto the surface of the component which is in contact with the liquid during the distillation/fermentation process.

The term 'source of copper' is intended to mean preferably copper wires, more preferably of thickness ranging from 0.01 to 100 mm, preferably from 1 mm to 5 mm.

Preferably the copper is atomized/ionized, generating an electric arc at a temperature ranging from 500 to 15000° C., preferably of about 5000° C. The stage of atomization/ionization of the copper is effected preferably in the presence of a gas, more preferably chosen from among: compressed air, nitrogen, helium, xenon and other noble gases.

The stage of emission of the copper is preferably effected at a velocity of about 100 metres per second (m/sec), more preferably at a velocity ranging from 10 to 1000 m/sec.

As regards the nanoparticles of TiO2, preferably in the form of anatase, in a preferred embodiment of the invention, these are deposited onto the layer of nanostructured copper by the method of spin-coating, preferably followed by a treatment at high temperature.

In particular, the method of spin-coating is realized by using a solution, preferably alcoholic, of TiO2 (in the form of anatase), more preferably at a concentration ranging from 0.5 to 3 mg/ml, preferably from 1 to 1.5 mg/ml. Preferably, the particles of TiO2 are deposited on the nanostructured layer of copper at a velocity ranging from 300 to 1000 rpm, more preferably from 400 to 600 rpm, even more preferably at about 500 rpm, for a period of time ranging preferably from 3 to 10 seconds, more preferably of about 5 seconds.

According to a preferred embodiment of the invention, following the method of spin-coating a treatment is performed with a temperature ranging from 180 to 300° C., preferably from 180 to 250° C., more preferably at a temperature of about 200° C.

Said treatment allows a true entrapment of the nanoparticles of TiO2 between those of the copper. In other words, there is a partial sinking of the nanoparticles of TiO2 into the bed consisting of nanoparticles of copper.

The deposition of the nanoparticles of TiO2 can alternatively be achieved with any other method known in the sector for the appointed purposes. In particular, a method may be used chosen from among the group consisting of: electric arc, thermal embedding, laser assisted embedding, spatially controlled nanoembedding, sol-gel and spraying.

Alternatively it is possible to obtain a metallic component of a distillation and/or fermentation apparatus covered, totally or partially, with at least one layer of nanostructured copper and of nanoparticles of TiO2 by adding the TiO2 nanoparticles, preferably in powder form, directly onto the nanostructured copper layer and leaving the component thus treated at a temperature ranging between 50 and 600° C., more preferably of about 300° C. for a time ranging preferably from 10 to 90 minutes, more preferably 30 minutes. Preferably the high-temperature treatment is followed by rapid cooling of the component.

A further aspect, therefore, of the present invention concerns a metallic component of a distillation and/or fermentation apparatus covered, totally or partially, with at least one layer of nanostructured copper obtainable with a method described above, in particular with a method chosen from among the group consisting of: electric arc, thermal embedding, laser assisted embedding, spatially controlled nanoembedding, sol-gel and spraying, preferably electric arc.

In particular, the present invention concerns a metallic component of a distillation and/or fermentation apparatus covered, totally or partially, with at least one layer of nanostructured copper, obtainable with a method which specifies at least one stage of melting a source of copper; and/or at least one stage of atomization or ionization of the copper, and/or at least one stage of emission of the atomized/ionized copper onto said metallic component, preferably onto the surface of the component which is in contact with the liquid during the distillation/fermentation process.

In a preferred embodiment of the invention said metallic component of a distillation and/or fermentation apparatus covered, totally or partially, with at least one layer of nanostructured copper, further comprises nanoparticles of TiO2, preferably deposited on said layer of nanostructured copper by one of the methods described above.

According to a further preferred aspect of the present invention, said metallic component of a distillation and/or fermentation apparatus is preferably chosen from among the group consisting of: distillation trays, valves for distillation trays, structured packings or random packings, pot stills, pot still parts, dephlegmators, infusers, scrubber columns, evaporators, distillation columns, demisters, containers, tubes and valves for distillation plants, shell and tube heat exchangers, plate heat exchangers, reboilers, condensers, containers, filters, lyne arms and fermenters.

Alternatively said component is any operating unit (unitary operation) used for the production of spirit beverages.

Alternatively said metallic component is a column distillation apparatus, a packing distillation apparatus, a pot still or a heat exchanger.

A further subject of the present invention therefore consists of a distillation plate, a valve for a distillation plate, a structured or random packing, a pot still or pot still parts, a dephlegmator, an infuser, a scrubber column, an evaporator, a distillation column, a demister, a container, a tube or a valve for distillation plants, a shell-and-tube heat exchanger, a plate heat exchanger, a reboiler, a condenser, a container, a filter, a lyne arm or a fermenter for distillation and/or fermentation plants, in metallic material, covered, partially or totally, with a nanostructured layer of copper and possibly nanoparticles of TiO2 as described above.

Particularly preferred for the purposes of the present invention is a distillation plate, in metallic material, characterized by being covered, preferably, on the surface which is in contact with liquid (must) during distillation/fermentation, with a nanostructured layer of copper and possibly TiO2 nanoparticles. Preferably said covering is partial or total.

Said covering (or facing) comprising at least one layer of nanostructured copper and possibly particles of TiO2 is preferably obtained by one of the methods mentioned above. Preferably the electric arc is used for the purpose of obtaining the nanostructured copper layer and the spin-coating followed by the high-temperature treatment for the purpose of obtaining the deposition of the nanoparticles of TiO2.

In particular, the distillation plate of the present invention is obtainable by subjecting the plate or at least a part of the surface which is in contact with the liquid (must) during distillation/fermentation, to at least one stage of melting a source of copper; and/or at least one stage of atomization or ionization of the melted copper, and/or at least one stage of emission of the atomized/ionized copper onto the component or onto said surface.

Said distillation plate is preferably made of copper and/or of stainless steel.

The distillation plate of the present invention is preferably suitable for being used in a distillation column and/or in a distillation apparatus.

A further subject of the present invention is therefore constituted by a distillation column comprising at least one plate according to the present invention.

A further subject of the present invention is a distillation apparatus comprising at least one distillation column and/or one distillation plate according to the present invention.

Preferably the distillation which is referred to is the alcoholic distillation of beverages, preferably chosen from among the group consisting of: rum, whisky, cognac, grappa, brandy, vodka, tequila, raki, ouzo, whiskey, bourbon, aquavit, extra neutral alcohol, neutral alcohol, and in general every other spirit beverage or alcohol hereafter added to a beverage. Alternatively the distillation which is referred to is any process which has as its result the production of ethyl alcohol starting from an organic raw material, or the fractionated distillation of mixtures of hydrocarbons such as petroleum.

The method of the present invention can also be used to cover a metallic surface suitable for absorbing pollutants, preferably sulphur-based, present in hydrocarbon solutions such as petroleum.

The method of the present invention makes it possible, with particular reference to the industry of the production of spirit beverages, to significantly increase the active surface area of the metal onto which the nanostructured copper layer is deposited.

The term 'active surface' is intended to mean the surface which is capable of interacting with the liquid and/or gaseous current in any stage of the production process and in particular during the stages of fermentation, distillation and packing and/or in any intermediate stage. In particular, the method of the present invention makes possible a considerable increase in the ratio (H) between the active surface area and the geometric surface area.

In the context of the present invention, this parameter indicates how large an active surface area it is possible to obtain by depositing a covering (or facing) comprising at least one nanostructured copper layer for a given available geometric surface area, and provides an immediate indication of the gain in active surface area obtainable.

For example, as regards a distillation plate made of copper, the activity of the copper is proportional to the contact area between the plate and the product being distilled, which, in the typical case where the plate is made from commercial sheet metal, we assume coincides with the geometric area of the plate. In this case evidently it will be H=1. By covering the same commercial plate using the method of the present invention, a value of H is observed ranging from 5 to 10, preferably from 7 to 8. In other words, the active surface area is increased by at least 7, preferably 8 times.

With particular reference to the distillation sector, preferably the distillation of beverages, the component of a distillation apparatus of the present invention demonstrates a greatly enhanced adsorption capacity compared with components, for example of copper or stainless steel, obtained with traditional metallurgical techniques. In fact, by using the metallic components of the present invention it is possible to maximize the removal of mercaptans, sulphides, carbamates and other undesired compounds during the process of distillation/fermentation which, as previously emphasized, alter the flavour of the distillate/fermentate and are hazardous to public health.

Furthermore, the metallic components obtained by the method of the present invention are advantageously self-cleaning.

In fact, when a metallic component covered by at least one nanostructured copper layer and by nanoparticles of TiO2 is exposed to a source of UV rays, the nanoparticles of TiO2 are capable of degrading the mercaptans, sulphides, ethyl carbamate and in general the undesired compounds present in the mixture during the process of distillation/fermentation.

In this way, it is possible to avoid long and costly cycles of cleaning distillation/fermentation apparatus which has surfaces of normal copper saturated with mercaptans, sulphides, ethyl carbamate and other undesired compounds, thus reducing energy consumption for washing cycles by about 50%.

This also implies a significant reduction in environmental pressures, in terms of eco-efficient process and product innovation, since the metallic components of the present invention are capable, once exposed to UV rays, of removing in a more effective and enhanced manner substances such as mercaptans, sulphides and ethyl carbamates and, being self-cleaning and self-regenerating, enable a significant saving of energy expended on cleaning operations, and a smaller pollutant load for the effluents.

Also, we should not underestimate the fact that the washing cycles which are obligatory for distillation apparatuses characterized by normal copper surfaces (i.e. those currently used), make it necessary to stop the distillation/fermentation process, with repercussions from a commercial point of view.

Furthermore, the washing cycles, being performed with aggressive chemical substances, corrode the copper part treated which inevitably becomes thinner and must therefore be more frequently replaced because its mechanical properties are altered.

EXAMPLE

The method of the present invention was applied using sheets (plates) of 99.9% pure copper, divided into strips with dimensions 1×1×0.4 cm (i.e. about 4.88 0.15 cm2).

Some strips of copper were surface-coated with a nanostructured layer of metallic copper by means of the electric arc technique which allowed copper to be sprayed onto the smooth copper surface so as to obtain nanoparticles of copper with dimensions of about 20-40 nanometres in diameter.

Electric arc technology is a "cold procedure" and the temperature of the target to be coated (covered) can be kept low during spraying, avoiding both metallurgical transformations, and the deformation of the base metal. The electric arc technique requires the use of two electrically conductive wires, simultaneously fed towards each other, so as to form between them an electric arc which develops a temperature of about 5000° C.

The heat developed causes the melting of the ends of the wires.

A jet of compressed gas (usually compressed air) is used to atomize the melted copper and project it towards the target (in this case the surface of the copper plate) at a velocity greater than 100 metres per second.

The combination of high temperature and velocity of the particles enables the creation of facings (coverings) with high productivity and a low level of porosity, i.e. with a large available contact area and structurally compact. The copper plates covered by the method of the present invention were morphologically analysed under an electron microscope, in particular with FESEM (Field-Emission Scanning Electron Microscope) instrumentation combined with the EDX technique which makes it possible to assess the morphology of the surfaces and their chemical composition. In particular, the FESEM technique was applied by the use of a Zeiss FESEM Sigma VP microscope. To obtain the FESEM images, voltages ranging from 5 to 20 kV and a current band of 2.4 A were used.

Figure 1:
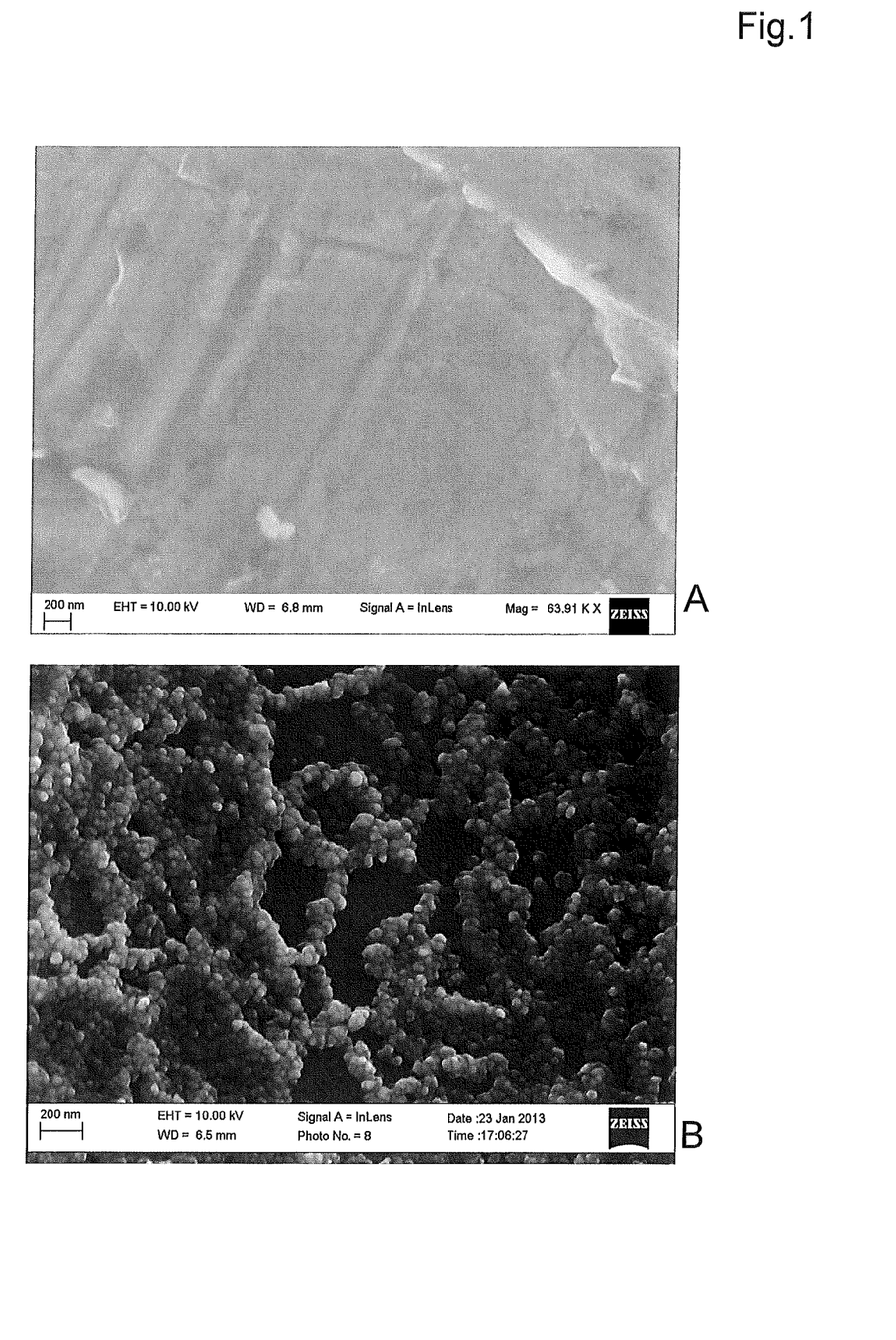
FIG. 1 shows an image, acquired by scanning electron microscope, of an ordinary copper plate (FIG. 1A, the control) and a copper plate covered with a nanostructured copper layer in accordance with the present invention (FIG. 1B)

FIG. 1 shows images acquired using the electron microscope, of a normal copper plate (i.e. the control, FIG. 1A) and a copper plate covered with a layer of nanostructured copper according to the method of the present invention (FIG. 1B); As may be noted the method of the present invention generates a nanostructured micro-covering of copper which entails an increase in the active surface area of about 5 times compared with a normal copper surface not subjected to the method of the present invention.

The surfaces of the copper plates covered by the nanostructured layer of metallic copper were analysed with the aim of assessing their behaviour in conditions comparable to those encountered in the distillation process. Normal copper plates were used as control samples.

In particular, with the object of assessing whether the active surface area obtained by generating the nanostructured layer of metallic copper made it possible to obtain a substantial increase in adsorption at the expense of the undesired substances during distillation, the copper plates covered with the layer of nanostructured metallic copper and the normal copper plates were kept at 70-80° C. in a hydroalcoholic solution of mercaptans and sulphurated substances.

In particular, the interaction tests were performed in a 250 ml volume of a 10% solution of ethanol containing a concentration of 0.01 M of each of the following contaminants: ethyl mercaptan 97% ($C_2H_6S$, MW=62.13 g/mol), 1-propyl mercaptan 99% ($C_3H_8S$, MW=76.16 g/mol), dimethyl disulphide 99%, dimethyl disulphide 98.0 ($C_2H_6S_2$, MW=94.20 g/mol), dimethyl trisulphide ($C_2H_6S_3$, MW=126.26 g/mol) and ethyl carbamate 99% ($C_3H_7NO_2$, MW=89.09 g/mol).

The iteration tests were performed at 70-80° C. for 1 hour in a 500 ml flask mounted on a rotating evaporator (Laborota 4000-Efficient) using as heat source a heating jacket (plate).

Figure 2:
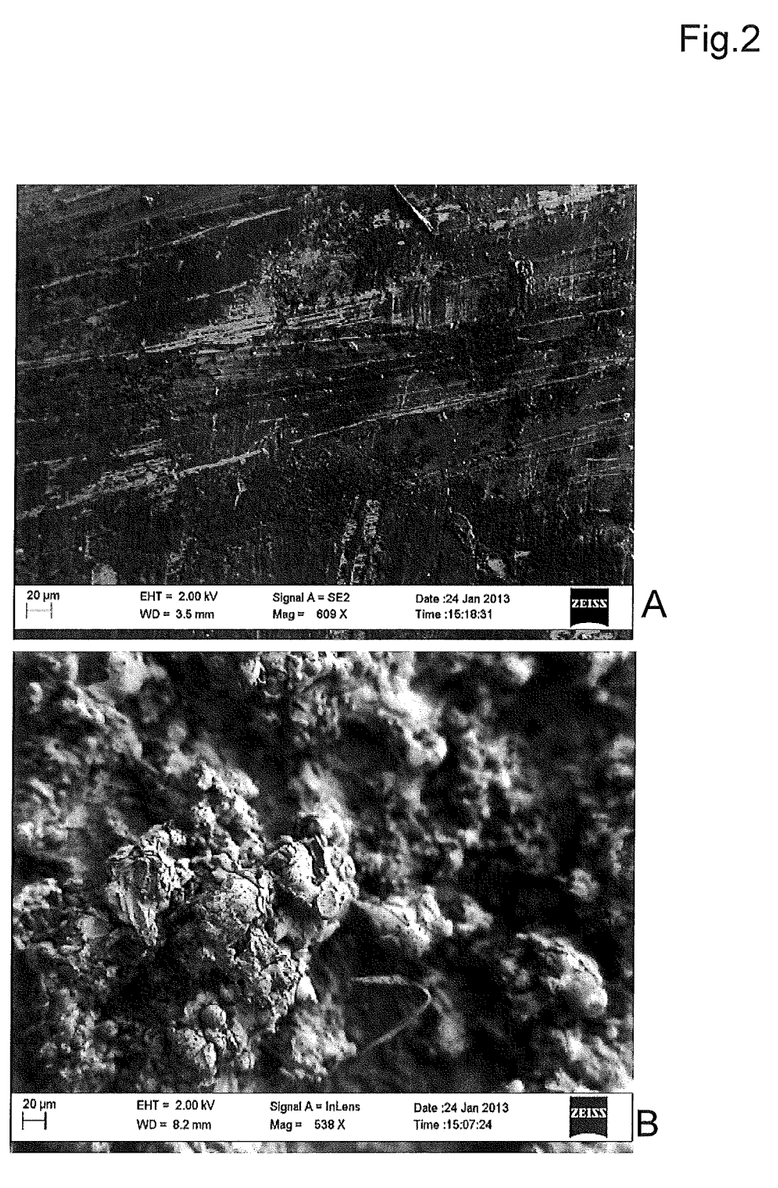
FIG. 2 shows an image, acquired by scanning electron microscope, of an ordinary copper plate (FIG. 2A, the control) and a copper plate covered with a nanostructured copper layer (FIG. 2B, the present invention) following interaction tests with the undesired substances.

The results are shown in FIG. 2 and in Table I below:

TABLE I

| Absolute quantity on plate 1 × 1 × 0.4 cm of normal copper | Q/A (mg/cm2) | Absolute quantity on plate 1 × 1 × 0.4 cm of copper covered with a nanostructured layer of metallic copper | Q/A (mg/cm2) |
|---|---|---|---|
| 5.0 mg | 1H.0 | 17.5 mg | 6.2 |
| 6.1 mg | 1.2 | 19.2 mg | 6.9 |
| 7.8 mg | 1.6 | 22.9 mg | 8.2 |

In particular, Table I states the quantities of substances adsorbed per cm2 of surface area after 24 hours of treatment.

The ratio of the absolute quantities demonstrates that with the method of the present invention the surface of active copper against the undesired substances that are liberated during distillation, such as mercaptans, sulphides and ethyl carbamate is 3.2. As regards the ratio between the quantities per square centimetre, the value rises to 5.6. The results therefore demonstrate that the surface of nanostructured copper is capable of absorbing sulphated compounds in quantities far greater than a normal copper surface not subjected to the method of the present invention and commonly used for making distillation apparatuses. This implies a useful life for distillation/fermentation plants made with the method of the present invention triple that of those in common use.

It was explained above that during distillation the copper performs an important function of capturing substances such as mercaptans, sulphides and ethyl carbamate which alter the flavour of the distillate. However, once copper surfaces have been saturated with these compounds they are no longer capable of performing this function, but on the contrary begin to release nitrogenous copper compounds which can in turn generate ethyl carbamate. The need therefore arises to develop a method which makes it possible to clean the surfaces of copper saturated with compounds such as mercaptans, sulphides and ethyl carbamate which is simple and quick, so as to have as little impact as possible on the distillation process, on the economics of production and on the environment.

To this end, nanoparticles of TiO2 (anatase) of dimensions 20-100 nm in diameter are deposited on the copper plates covered by the method of the present invention. In particular, the covering was realized with the technique of spin-coating using a solution of TiO2 1 mg/ml in ethanol. The spin-coating was performed for 5 seconds at 500 rpm using the system Specialty Coating Systems G3P-8.

After this treatment the plates were kept for about two hours at 200° C. with the object of fixing the particles of TiO2 to the layer of nanostructured copper.

Following this treatment the particles of TiO2 remain trapped between the nanoparticles of copper.

Figure 3:
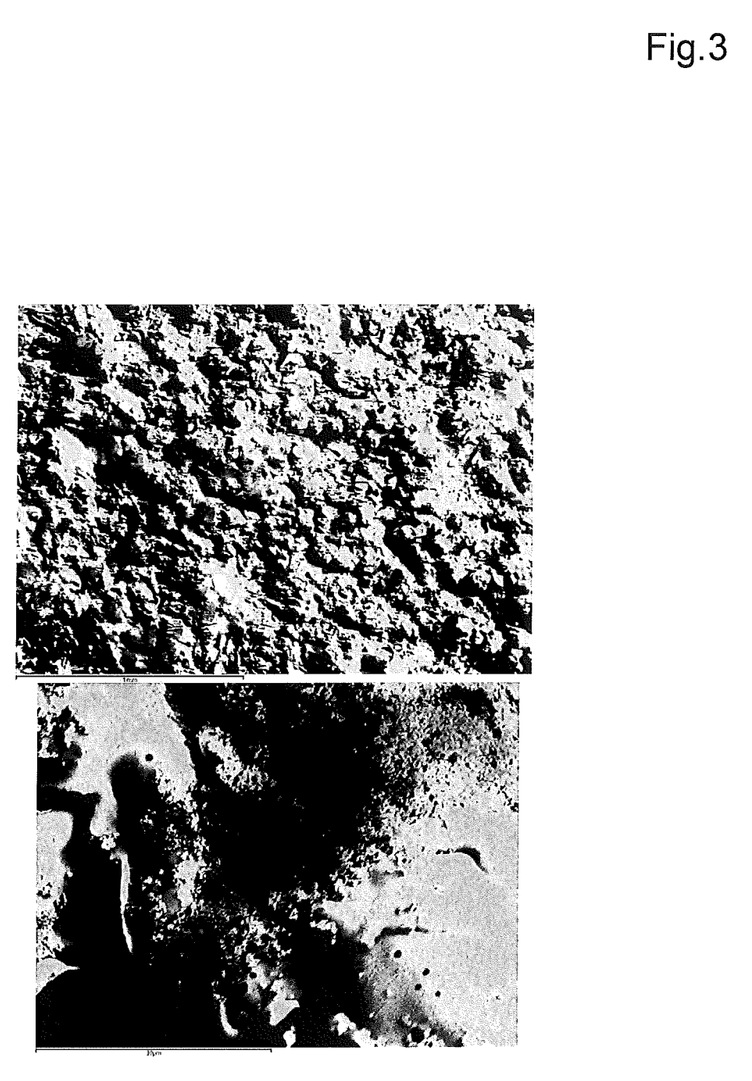
FIG. 3 shows an image, acquired by scanning electron microscope, of a copper plate covered with a nanostructured copper layer containing nanoparticles of TiO2 in accordance with the present invention (FIG. 3)

FIG. 3 shows images created with the technique FESEM-EDX of a copper plate covered by the method of the present invention and subjected to spin-coating to deposit the particles of TiO2, which under the electron microscope, using the EDX technique to display the titanium, are visible as red spots. It should be noted that the nanoparticles of TiO2 do not completely cover the copper surface but are deposited in small agglomerations, thus allowing the copper surface exposed to the distillate/fermentate to interact with the undesired substances present in the mixture.

Figure 4:
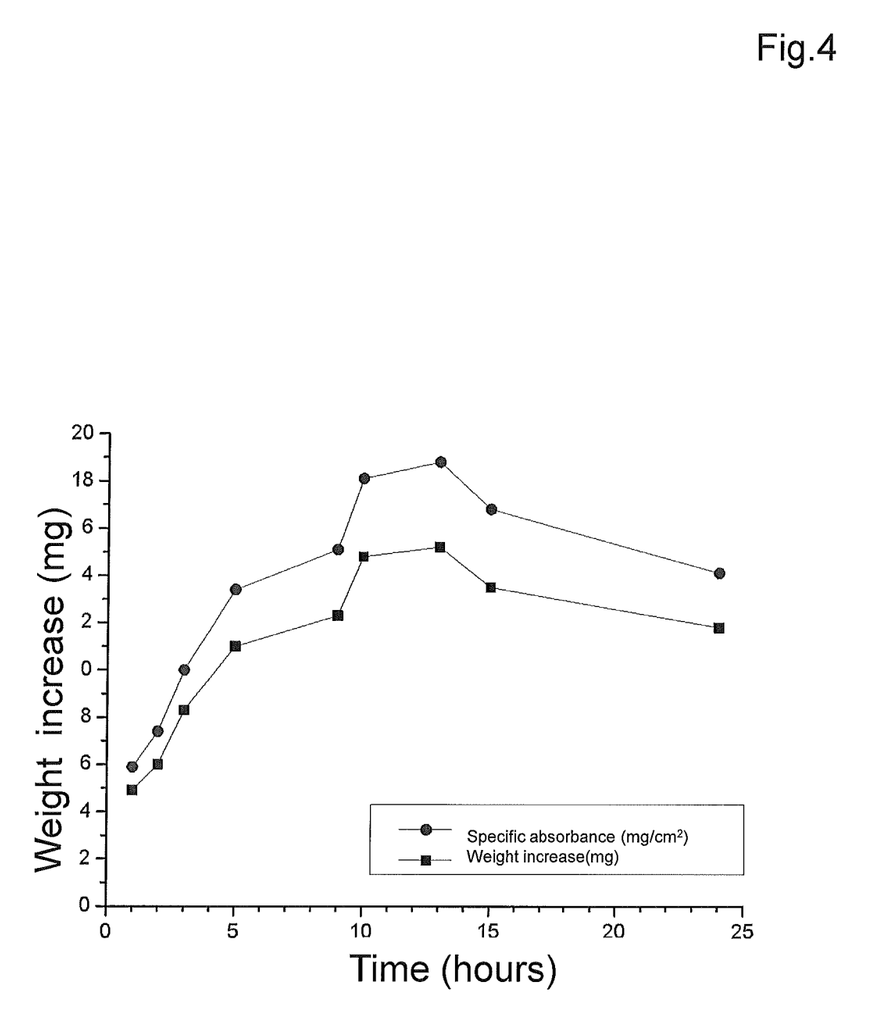
FIG. 4 shows the increase in weight of the copper plate covered with nanostructured copper and nanoparticles of TiO2 (due to the presence of mercaptan compounds, sulphides and ethyl carbamate) according to the present invention as a function of time, expressed in absolute terms and per unit area.

The deposition of particles of TiO2 onto the nanostructured copper covering does not interfere with its capacity to capture the undesired substances during distillation. In fact, FIG. 4 shows the increase in the weight of the copper plate covered with nanostructured copper and nanoparticles of TiO2 as a function of time, expressed in absolute terms and per unit area.

In order to verify that the particles of TiO2 deposited on the copper plate covered with the nanostructured copper layer were capable of degrading organic substances such as mercaptans and/or ethyl carbamate, the plate was put into a methylene blue solution and irradiated for 3 hours with a mercury vapour UV lamp of 400 W power. At regular intervals the absorption spectrum corresponding to methylene blue was measured (the reading was taken from 200 to 800 nm).

Figure 5:
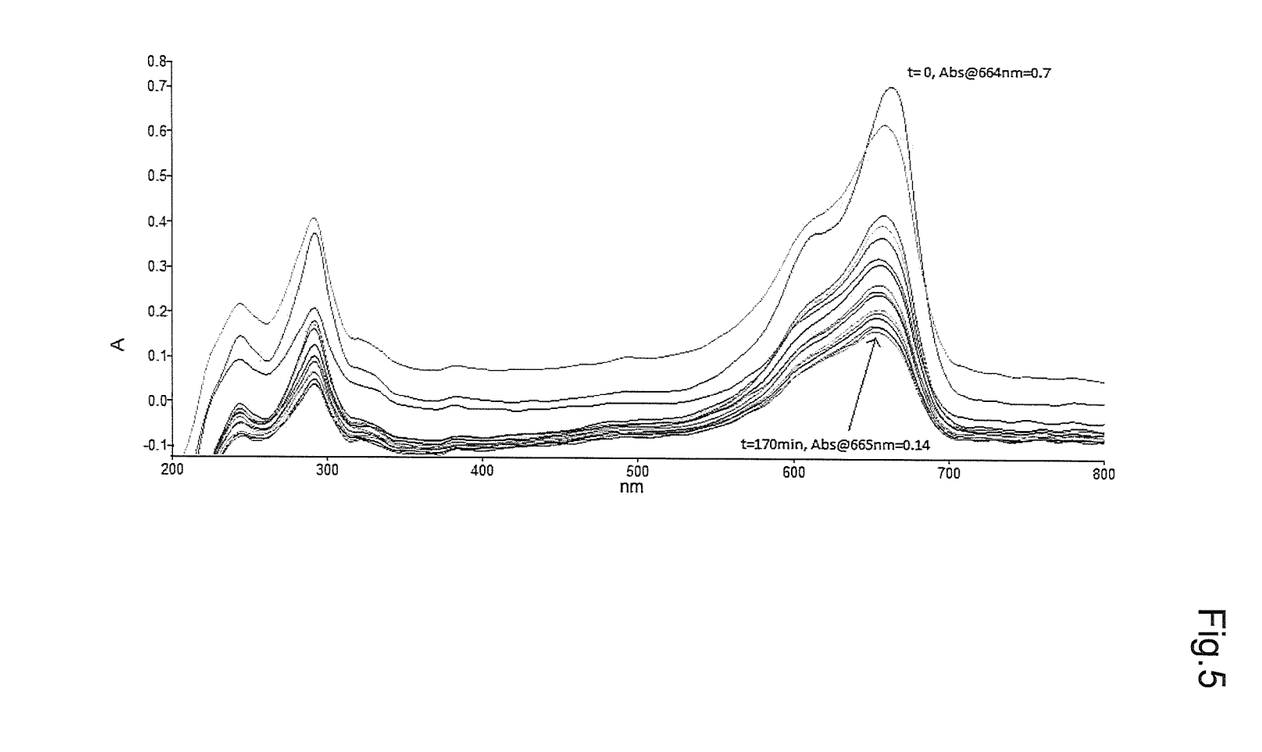
FIG. 5 shows, through the decomposition reaction of methylene blue, the photo-catalytic capacity of the copper plate covered with a nanostructured copper layer containing nanoparticles of TiO2 according to the present invention. The decomposition of the methylene blue is determined through the variation in its absorption spectrum, as a function of the time of irradiation with a UV lamp, of a solution of methylene blue in contact with a copper plate covered with nanostructured copper and nanoparticles of TiO2.

The results shown in FIG. 5 demonstrate that the absorption peaks typical of methylene blue decrease progressively with the time of irradiation with the UV lamp, revealing the catalytic activity of the particles of TiO2 in the degradation of this compound. The nanoparticles of TiO2 deposited on the nanostructured copper covering can also perform catalytic degradation activity on the substances present and thus degrade undesired substances such as mercaptans, sulphides and ethyl carbamate which are deposited in the course of distillation onto the covering itself, saturating it.

Figure 6:
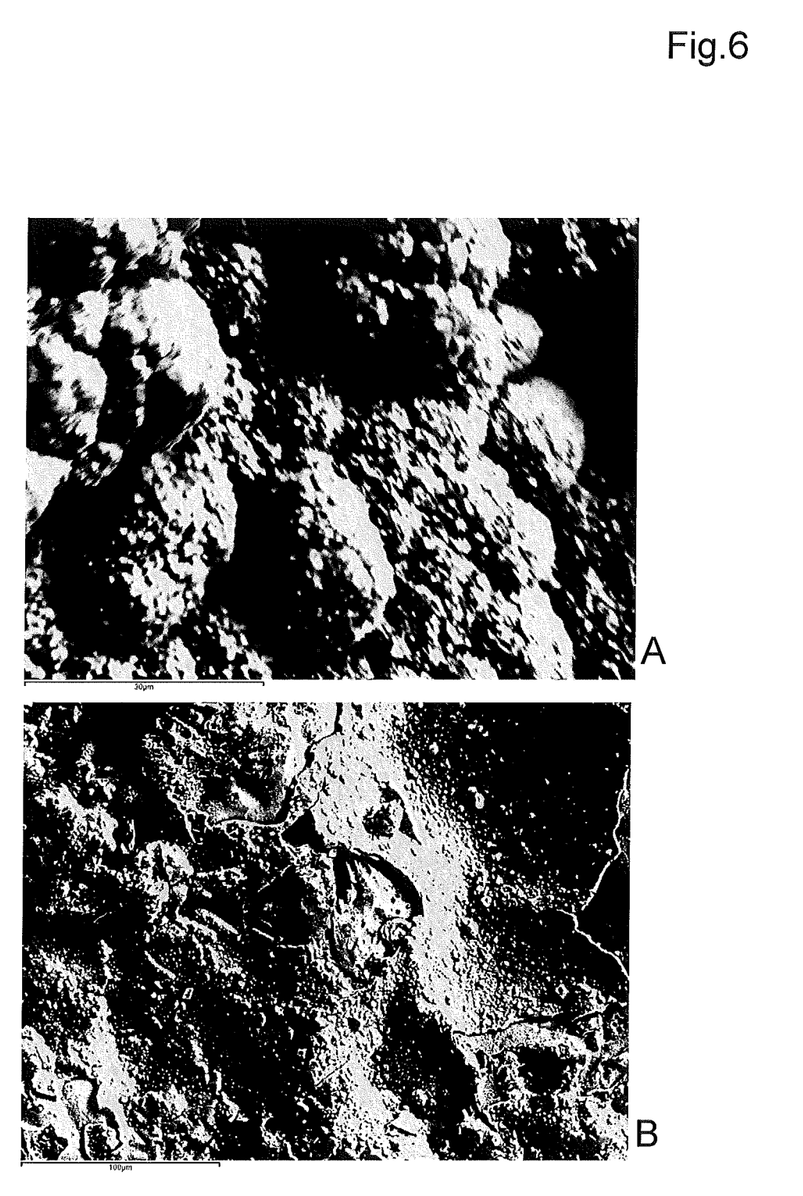
FIG. 6 shows scanning electron microscope images of a copper plate covered with nanostructured copper and nanoparticles of TiO2, said plate being saturated with sulphurated substances according to the present invention, before (FIG. 6A) and after (FIG. 6B) treatment with UV rays which degrade the layer formed by the adsorbed sulphurated substances.

FIG. 6 shows the images of a copper plate covered by a nanostructured copper layer and nanoparticles of TiO2 according to the present invention and saturated by sulphurated substances as previously described. FIG. 6A demonstrates that the nanostructured copper covering optimally performs its role of capturing sulphurated compounds, ending up completely covered with them. The presence of compounds containing sulphur is confirmed by the EDX analysis and evidenced by the yellow covering which, as is observed in the microscope image, completely covers the metallic surface.

Following irradiation with UV light (7 hours) deterioration of the polluting substances occurs. As shown in FIG. 6B, the layer of sulphurated compounds no longer covers the base material homogeneously, but there are areas where the copper surface goes back to being available for re-use.

The invention claimed is:

1. A metallic component of a distillation or fermentation apparatus for removing ethyl carbamate during distillation and/or fermentation, said component being selected from a group consisting of distillation trays, valves for distillation trays, structured packings or random packings, pot still or pot still parts, dephlegmators, infusers, scrubber columns, evaporators, distillation columns, demisters, containers, tubes and valves for distillation apparatus, shell and tube heat exchangers, plate heat exchangers, reboilers, condensers, filters, lyne arms and fermenters, wherein said component is covered, totally or partially, by at least one layer having mean thickness ranging from 0.25 to 1 mm consisting of nanostructured copper and optionally $TiO_2$ nanoparticles.

2. The metallic component according to claim 1, wherein said layer of nanostructured copper consists of copper nanoparticles having a diameter ranging from 10 to 50 nm.

3. The metallic component according to claim 1, wherein the $TiO_2$ nanoparticles have a diameter ranging from 50 to 200 nm.

4. The metallic component according to claim 1, wherein said metallic component is a copper and/or steel component.

5. The metallic component according to claim 1, wherein said at least one layer of nanostructured copper is obtainable by a method comprising at least one phase of atomization and/or ionization of metallic copper on said component.

6. The metallic component according to claim 1, wherein said at least one layer of nanostructured copper is obtainable by a method selected from the group consisting of: electric arc, thermal embedding, laser assisted embedding, spatially controlled nanoembedding, sol-gel, spraying and spin-coating.

7. The metallic component according to claim 1, wherein said $TiO_2$ nanoparticles are deposited on said layer of nanostructured copper by spin-coating.

8. The metallic component according to claim 7, wherein said spin-coating comprises a phase of using a $TiO_2$ solution wherein the concentration of $TiO_2$ ranges from 0.5 to 3 mg/ml.

9. The metallic component according to claim 7, wherein said $TiO_2$ nanoparticles are deposited on said layer of nanostructured copper at a velocity ranging from 300 to 1000 rpm for a period ranging from 3 to 10 seconds.

10. The metallic component according to claim 1, wherein said component is a distillation tray or a distillation column.

11. Distillation apparatus comprising a metallic component according to claim 1.

12. Fermentation apparatus comprising a metallic component according to claim 1.

13. A method of removing ethyl carbamate during distillation and/or fermentation of beverages comprising a step of utilizing a metallic component according to claim 1.

14. The metallic component according to claim 2, wherein said layer of nanostructured copper consists of copper nanoparticles having a diameter ranging from 20 to 40 nm.

15. The metallic component according to claim 3, wherein the $TiO_2$ nanoparticles have a diameter ranging from 80 to 150 nm.

16. The metallic component according to claim 8, wherein the concentration of $TiO_2$ ranges from 1 to 1.5 mg/ml.

17. The metallic component according to claim 7, wherein the spin-coating is followed by a treatment with a temperature ranging from 180 to 300° C.

18. The metallic component according to claim 7, wherein said $TiO_2$ nanoparticles are deposited on said layer of nanostructured copper at a velocity ranging from 400 to 600 rpm, for a period of 5 seconds.

* * * * *